US006963006B2

(12) United States Patent
Tsui et al.

(10) Patent No.: US 6,963,006 B2
(45) Date of Patent: Nov. 8, 2005

(54) PROCESS FOR THE PRODUCTION AND PURIFICATION OF BIS(TERTIARY-BUTYLAMINO)SILANE

(75) Inventors: Yin Pang Tsui, Carlsbad, CA (US); Thomas Elwood Zellner, Lehighton, PA (US); Rajiv K. Agarwal, North Wales, PA (US); Ravi Kumar Laxman, San Jose, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 120 days.

(21) Appl. No.: 10/342,930

(22) Filed: Jan. 15, 2003

(65) Prior Publication Data

US 2004/0138491 A1 Jul. 15, 2004

(51) Int. Cl.$^7$ ............................. C07F 7/02; C07F 7/10
(52) U.S. Cl. ..................................................... 556/410
(58) Field of Search ........................ 556/410, 10, 12, 556/412

(56) References Cited

U.S. PATENT DOCUMENTS

| | | | | |
|---|---|---|---|---|
| 4,304,805 A | * | 12/1981 | Packo et al. | 428/63 |
| 4,725,660 A | * | 2/1988 | Serita et al. | 528/28 |
| 5,874,368 A | | 2/1999 | Laxman et al. | 438/794 |
| 5,976,991 A | | 11/1999 | Laxman et al. | 438/786 |
| 6,180,810 B1 | * | 1/2001 | Gately | 556/410 |
| 2002/0180028 A1 | | 12/2002 | Borovik et al. | |

OTHER PUBLICATIONS

Radhamani et al., High Yield Room Temperature Synthesis and Spectral Studies of Tri(Amino)Silanes: (R2N)3SiH, Phosphorus, Sulfur and Silicon, vol. 66, 1992, pp. 297–300.*

Radhamani et al., A Convenient High Yield Room Temperature Synthesis of Mixed Tri(Amino)Silanes by Transamination of Tris(Dicyclohexylamino)Silane and Their Characterization, Phosphorus, Sulfur and Silicon, vol. 79, pp. 65–68.*
Radhamani et al., Phosphorus, Sulfur and Silicon, 1993, vol. 79, pp. 65–68.*
Penn et al., Industrial and Engineering Chemsitry Process Design and Development (1984), 23(2), 217–220.*
D. G. Anderson, et al., "Isopropyldisilylamine and Disilyl–t–butylamine: Preparation, Spectroscopic Properties, and Molecular Structure in the Gas Phase, Determined by Electron Diffraction," J. Chem. Soc. Dalton Trans., 1989, pp. 779–783.
D. G. Anderson, et al., "Die Strukur von gasförmigern und festern Chlorsilyl–N–N–dimethylamin," Angew. Chem., 98, 1986, No. 1, pp. 97–99, (Abstract).
K. N. Radhamani, et al., "A Convenient High Yield Room Temperature Synthesis of Mixed Tri(Amino)Silanes by Transamination of Tris(Dicyclohexylamino)Silane and Their Characterization," Phosphorus, Sulfur, and Silicon, vol. 79, pp. 65–68 (1993).
K. N. Radhamani, et al., High Yield Room Temperature Synthesis and Spectral Studies of Tri(Amino)Silanes: (R$_2$N0$_3$SiH, Phosphorus, Sulfur, and Silicon, vol. 66, pp. 297–300 (1992).
K. N. Radhamani, et al., "High Yield Room Temperature Synthesis and Spectral Studies of Tri(Amino)Silanes: (R$_2$N)$_3$SiH," Phosphorus, Sulfur, and Silicon, vol. 66, pp. 297–300 (1992).

* cited by examiner

Primary Examiner—Johann Richter
Assistant Examiner—Chukwuma Nwaonicha
(74) Attorney, Agent, or Firm—Rosaleen P. Morris-Oskanian

(57) ABSTRACT

A process for synthesizing an aminosilane compound such as bis(tertiarybutylamino)silane is provided. In one aspect of the present invention, there is provided a process for making bis(tertiarybutylamino)silane comprising reacting a stoichiometric excess of tert-butylamine with dichlorosilane under anhydrous conditions sufficient such that a liquid comprising the bis(tertiarybutylamino)silane product is produced.

20 Claims, 1 Drawing Sheet

PROCESS FOR THE PRODUCTION AND PURIFICATION OF BIS(TERTIARY-BUTYLAMINO)SILANE

BACKGROUND OF THE INVENTION

The present invention relates generally to a process and purification method for making an aminosilane. More particularly, the present invention relates to a process and purification method for making the aminosilane, bis(tertiarybutylamino)silane.

Silicon-nitrogen based compounds are used as precursors for depositing, via chemical vapor deposition or similar means, silicon nitride, silicon carbonitride, and silicon oxynitride films that can be used in semiconductor device fabrication. For example, silicon nitride has many applications in device fabrication because of its superior barrier properties and oxidation resistance. Typically, $NH_3$ and $Cl_2SiH_2$ mixtures are used to deposit silicon nitride via chemical vapor deposition at temperatures approaching 800° C. The volatile ammonium chloride ("$NH_4Cl$") and other chlorine by-products of this reaction can lead to particle formation and hazy films and can also deposit at the exhaust of the reactor tube. These deposits can cause wafer and pump damage.

The aminosilane, bis(tertiary-butylamino)silane, is a liquid chemical precursor for the chemical vapor deposition (CVD) of uniform silicon nitride, silicon oxynitride and silicon dioxide films. U.S. Pat. Nos. 5,874,368 and 5,976,991, which are assigned to the assignee of the present invention, describe CVD methods for preparing silicon and oxide containing films using the bis(tertiary-butylamino)silane (BTBAS). Bis(tertiary-butylamino)silane has the following chemical formula: $(t-C_4H_9NH)_2SiH_2$. The deposited films obtained using BTBAS as the precursor are free of ammonium chloride and chlorine contamination at relatively lower process temperatures, i.e., 500 to 800° C. Further, the BTBAS precursor does not contain direct Si—C bonds, and the resulting films are substantially free, or contain very low levels, of carbon. By contrast, analogous aminosilanes which contain ligands such as n-butylamines and tetrakis(dimethylamino)silane do not deposit carbon free films at the lower process temperature ranges and the film uniformities are relatively poorer.

The prior art is silent with regard to a process for the production of the aminosilane compound bis(tertiary-butylamino)silane. However, current production methods for aminosilane compounds typically involve one or more solvents. Prior to use, the solvent needs to be purified and dried to prevent the introduction of impurities in the end-product and dried to the prevent the newly-formed compound from hydrolyzing to siloxane and its respective amine. The articles, K. N. Radhamani et al., "High Yield Room Temperature Synthesis and Spectral Studies of Tri(amino)silanes: $(R_2N)_3SiH$", Phosphorous, Sulfur, and Silicon, Vol. 66 (1992), pp. 297–300 ("Radhamani I") and K. N. Radhamani et al., "A Convenient High Yield Room Temperature Synthesis of Mixed Tri(amino)silanes by Transamination of Tris(cyclohexylamino)silane and Their Characterization", Phosphorous, Sulfur, and Silicon, Vol. 79 (1993), pp. 65–68 ("Radhamani II"), describe similar reactions for the synthesis of triaminosilanes and mixed aminosilanes, respectively. Radhamani I describes reacting a secondary amine ($R_2NH$) with trichlorosilane to form $(R_2N)_3$ SiH and $3R_2NH\cdot HCl$ salt. Similarly, Radhamani II describes reacting dicyclohexylamine with trichlorosilane to form tris(dicyclohexylamino)silane and dicyclohexyamine.HCl salt. Both reactions are conducted at a temperature near room temperature under a nitrogen atmosphere using a benzene/n-hexane mix as the solvent. The benzene and n-hexane solvents were purified via distillation and dried via sodium wire prior to use within the reaction.

Accordingly, there is a need in the art to provide a process for the production and for the purification of the aminosilane bis(tertiary-butylamino)silane. There is also a need in the art for a safe industrial and cost-effective process to make and purify the aminosilane compound bis(tertiary-butylamino)silane at a high yield, less cycle time, lower process temperatures, less volatility, and in a single reaction vessel. It is thus surprising and unexpected to produce the aminosilane compound bis(tertiary-butylamino)silane compounds at relatively high yields, lower process temperatures, and without the need for a solvent.

All references cited herein are incorporated herein by reference in their entirety.

BRIEF SUMMARY OF THE INVENTION

The present invention is directed, in part, to a method for the production and purification of the aminosilane, bis(tertiary-butylamino)silane. Specifically, in one aspect of the present invention, there is provided a process for preparing an aminosilane compound comprising reacting a stoichiometric excess of at least one amine selected from the group consisting of secondary amines having the formula $R1_2NH$, primary amines having the formula $R2NH_2$ or combinations thereof with at least one chlorosilane having the formula $R3_nSiCl_{4-n}$ under anhydrous conditions sufficient such that a liquid comprising the aminosilane product and an amine hydrochloride salt is produced wherein R1 and R2 can each independently be a linear, cyclic or branched alkyl group having 1 to 20 carbon atoms; R3 can be a hydrogen atom, an amine group, or a linear, cyclic or branched alkyl group having 1 to 20 carbon atoms; and n is a number ranging from 1 to 3.

In yet another aspect of the present invention, there is provided a process for making a bis(tertiarybutylamino)silane product comprising: reacting tert-butylamine with dichlorosilane under anhydrous conditions sufficient such that a liquid comprising said bis(tertiarybutylamino)silane product and a tert-butylamine hydrochloride salt is produced; passing the liquid through a filter to provide a tert-butylamine hydrochloride salt cake and a filtered liquid; and purifying the filtered liquid to provide the bis(tertiarybutylamino)silane product.

In still a further aspect of the present invention, there is provided a process for making a bis(tertiarybutylamino)silane product having a chloride level of 15 ppm or below, the process comprising: reacting tert-butylamine with dichlorosilane under anhydrous conditions sufficient such that a liquid comprising the bis(tertiarybutylamino)silane product and a tert-butylamine hydrochloride salt is produced; passing the liquid through a filter to provide a tert-butylamine hydrochloride salt cake and a filtered liquid; rinsing the tert-butylamine hydrochloride salt cake with tert-butylamine wherein at least a portion of the tert-butylamine rinse is used as at least a portion of the tert-butylamine in the reacting step; and purifying the filtered liquid to provide the bis(tertiarybutylamino)silane product.

In a further aspect of the present invention, there is provided a process for making a bis(tertiarybutylamino)silane product comprising reacting a stoichiometric excess of tert-butylamine with dichlorosilane under anhydrous conditions sufficient such that a liquid comprising the bis(tertiarybutylamino)silane product is produced.

These and other aspects of the invention will become apparent from the following detailed description.

DETAILED DESCRIPTION OF THE INVENTION

Figure 1:
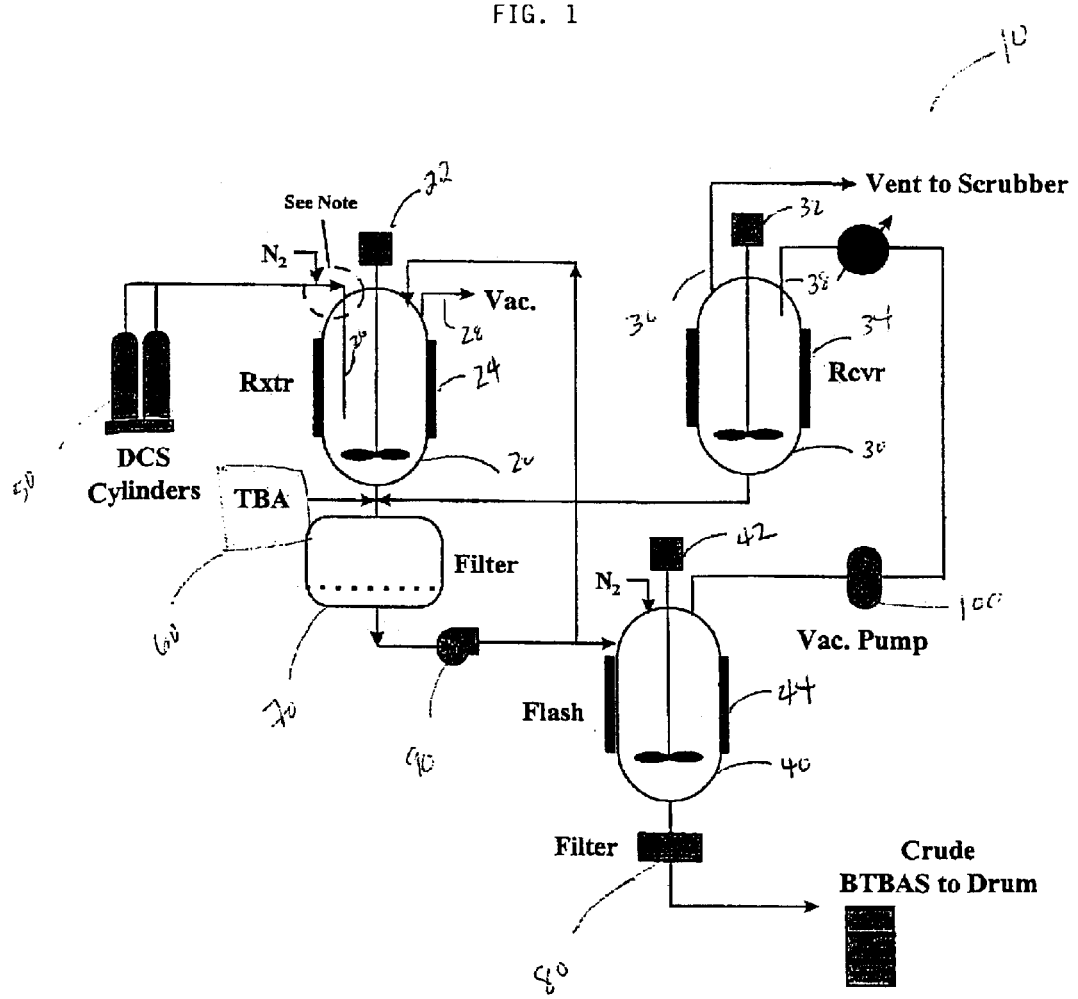
FIG. 1 provides an illustration of the system used in one embodiment of the method of the present invention.

The present invention is directed to a method for the production and purification of an aminosilane compound, particularly bis(tertiary-butylamino)silane (BTBAS). Unlike prior methods of making aminosilane compounds using a solvent, the present invention uses one of the reagents, the amine, as the solvent for the reaction. Further, certain aspects of the present invention may facilitate the removal of the reaction by-product, the amine hydrochloride salt from the aminosilane-containing crude liquid such that sublimation of the salt in subsequent process steps is minimized. This allows for a higher purity level of the aminosilane compound than was attainable heretofore. In addition, the present invention may also provide a more cost-effective process for an aminosilane compound through the recycle, recovery, and reuse of the amine reagent in subsequent reactions.

Although not intending to be bound by theory, it is believed that the present invention involves the reaction between at least one amine reagent and at least one chlorosilane reagent dispersed in a reaction mixture containing the amine. The amine source can be a secondary amine $R1_2NH$ or a primary amine $R2NH_2$ wherein R1 and R2 can be a linear, cyclic or branched alkyl group having 1 to 20 or preferably 1 to 10 carbon atoms. The amine used is preferably one that remains a liquid at reaction temperatures and pressures and produces an amine hydrochloride salt that is insoluble in the liquid reaction product. Exemplary secondary amines include dialkyl, diaryl, and aryl alkyl amines. Exemplary primary amines include tertiary butylamine. A preferred alkyl amine source is the primary amine tertiary butylamine (TBA). The chlorosilane reagent can be a compound having the formula $(R3)_nSiCl_{4-n}$ wherein R3 can be a hydrogen atom, an amine group, or a linear, cyclic or branched alkyl group having 1 to 20 or preferably 1 to 10 carbon atoms and n is a number ranging from 1 to 3. A preferred chlorosilane reagent is dichlorosilane (DCS).

In certain embodiments, it may be preferable that at least one of R1, R2, and/or R3 substituents in the amine and/or chlorosilane reagent be less sterically hindered. The term "sterically hindered" as used herein relates to radical groups that can impede a given reaction with another molecule by virtue of its size. Some non-limiting examples of sterically hindered alkyl groups include large primary (1°) alkyl groups such as octadecyl or nonadecyl; secondary (2°) alkyl groups such as isopropyl, isobutyl, or isopentyl; or tertiary (3°) alkyl groups such as tert-butyl ("t-butyl") or tert-pentyl ("t-pentyl").

The amine is present in the reaction mixture in an amount in excess of a stoichiometric amount and may act as both the reagent and the solvent within the reaction. The dual use of the amine as both the solvent and reagent provides many advantages over prior art methods involving a solvent. First, dual use of the amine ensures that the reaction is driven to completion. This avoids the potential for any unreacted chlorosilane reagent to remain within the solvent after the reaction is completed. Second, the amine that is removed from the liquid reaction product or subsequent process steps can be reused as a reagent in the reaction step.

The product of the reaction between the amine and the chlorosilane is a crude liquid that contains, inter alia, the aminosilane compound, the amine, and an amine hydrochloride salt. The reaction occurs rapidly, is exothermic, and is selective in the formation of the aminosilane compound. In a preferred embodiment of the present invention, the reagents TBA and DCS are reacted to form a liquid containing BTBAS. This liquid which is referred to herein as "BTBAS crude" contains, inter alia, BTBAS, TBA, and tert-butylamine hydrochloride (TBA.HCl) salt. The anticipated yield of BTBAS within the BTBAS crude ranges from 80% or greater, more preferably 90% or greater of the theoretical yield. The BTBAS crude is preferably subjected to further processing such as purification prior to use, for example, as a precursor for chemical vapor deposition. When used as a precursor, it is desirable that the amount of chloride present within the purified BTBAS is 15 ppm or less to avoid the introduction of chloride contaminants in a CVD deposited film.

An example of the process chemistry for one particular embodiment of the present invention is presented in the following equation:

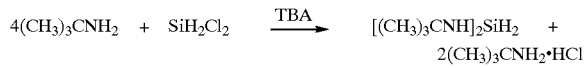

Referring to the above equation, a BTBAS crude liquid is formed by the reaction of tertiary butylamine (TBA) and dichlorosilane (DCS). Four moles of TBA are consumed for each mole of DCS reacted. An amount of TBA in excess of the stoichiometric amount is used as the solvent. The BTBAS crude liquid contains two moles of tert-butylamine hydrochloride salt (TBA.HCl) which were formed for each mole of dichlorosilane (DCS) reacted.

As mentioned previously, an aminosilane compound is formed by the reaction between at least one amine reagent and at least one chlorosilane reagent wherein at least one amine reagent is present in the reaction mixture in an amount in excess of the stoichiometric amount. In one aspect of the present invention, at least a portion of the amine added to the reactor is recycled from prior reactions such as, for example, the amine rinse used to rinse the salt cake from prior reactions and the amine separated from the crude liquid. In certain preferred embodiments, the reagents, particularly the chlorosilane reagent, may be of higher purity, preferably 98% pure or greater, to minimize the amount of impurities that can result in the aminosilane-containing crude. In embodiments wherein the chlorosilane reagent is DCS, the DCS reagent may contain the impurities mono-chlorosilane and tri-chlorosilane present in an amount of 1 weight percent or less each.

The reaction mixture may be agitated to enhance the contact between the amine and the chlorosilane reagents. Agitation may be achieved, for example, by ultrasonic energy or mechanical agitation. In embodiments wherein the mixture is mechanically agitated, the reactor stirrer may be equipped with a turbine or a gas entrainment impeller.

The reaction is conducted under anhydrous conditions to avoid hydrolysis of the chlorosilane reagent and the aminosilane product. In this connection, the reactor system is thoroughly dried via heat, vacuum, or other means prior to conducting the reaction. The reaction is conducted at a temperature ranging from −10 to 50° C., preferably from 0 to 35° C. Since the reaction is exothermic, the temperature may be maintained by cooling the reactor using a reactor jacket or similar means.

In a preferred embodiment of the present invention, the chlorosilane reagent may be introduced to the reaction mixture as a liquid or a vapor. In embodiment where the chlorosilane reagent is added as a vapor, a non-reactive gas such as nitrogen or an inert gas may be employed as a carrier gas to deliver the vapor to the reaction mixture. The chlorosilane reagent is fed to the reaction mixture until the desired conversion of the amine to the liquid containing the aminosilane product, or crude liquid, has been achieved. In certain embodiments, the conversion is limited by the ability to adequately suspend the byproduct amine hydrochloride salt within the crude liquid. In alternative embodiments, the reaction may be run in a continuous manner by replenishing the chlorosilane and/or amine reagents and removing the reaction products such as the byproduct salt and the crude liquid from the reactor.

In one aspect of the present invention, the reactor contents are passed through at least one filter to substantially remove the byproduct salt from the crude liquid. Suitable filtration media are composed of a material that will not react with the crude or any of the components contained therein such as a ceramic, glass frit, or certain metals. A finer-sized mesh filter may be preferred, for example a 0.2 to 0.5 micron mesh filter, to minimize the possibility of the by-product salt remaining in the filtered liquid. The filtration step(s) can be conducted under vacuum to assist in extracting the salt from the crude liquid. It is preferable the filtration process be conducted at a temperature ranging from 0 to 30° C. to prevent the salt from subliming within the crude liquid. The salt cake formed on the surface of the filter can be rinsed with the amine reagent such as TBA to recover further aminosilane product such as the BTBAS contained within the crude. This amine rinse may be used as feed for subsequent reactions. In some embodiments, the amount of amine hydrochloride salt remaining within the crude after filtration is low enough to allow for purification processes involving higher process temperatures, i.e., ranging from 100 to 180° C.

As mentioned previously, the crude liquid may also contain a certain amount of the amine. The amine may be removed or separated from the crude liquid, for example, by evaporation or other means. In one embodiment, the crude liquid is heated to a temperature at or above the vaporization temperature of the amine. The amine reagent is vaporized and condensed into a collection vessel. The amine within the collection vessel may be used as the amine reagent in the reaction step. A vacuum may be applied to assist the removal of the amine from the crude liquid. The amount of the amine remaining in the crude liquid after evaporation and/or other removal processes is preferably 10 weight percent or below. The crude liquid may be subjected to filtration prior to and/or after removal of the amine from the crude. In one particular embodiment, the TBA is evaporated from the BTBAS crude liquid prior to filtration to remove the TBA.HCl byproduct salt.

The crude liquid containing the aminosilane is purified by one or more processes to substantially extract the aminosilane product contained therein. The reaction conditions of temperature and pressure for the purification of the crude vary depending upon the purification process used. Examples of suitable purification processes include, but are not limited to, distillation, evaporation, membrane separation, extraction, and combinations thereof. In one particular embodiment, the BTBAS crude is purified via distillation to extract the BTBAS contained therein. In these embodiments, the pressure can vary considerably from atmospheric to full vacuum and the temperatures can vary considerably from 0 to 180° C. or preferably from 70 to 90° C. In one embodiment of the present invention, the distillation is conducted at a pressure ranging from 40 to 100 torr, preferably 40 to 60 torr and a temperature ranging from 70 to 90° C.

FIG. 1 provides an illustration of a system 10 used to synthesize BTBAS using TBA and DCS as the reagents in accordance with one embodiment of the method of the present invention. System 10 has a reactor vessel 20, a receiver vessel 30, and a flash vessel 40. Vessels 10, 20, and 30 are in fluid communication with each other and are each equipped with a mechanical agitator 22, 32, and 42, respectively, and a heating/cooling jacket 24, 34, and 44, respectively. Vessels 20 and 40 are in fluid communication with a nitrogen gas source to allow for the dip tube 26 and vessel 40 to be nitrogen purged. Reactor vessel 20 is charged with a stoichiometric excess amount of liquid TBA from supply tank 60 shown. At least a portion of the TBA reagent can also be supplied from vessels 30 and 40. The reagent DCS 50 is housed in a pair of gas cylinders and is supplied as a vapor to reactor vessel 20 through dip tube 26. At the onset of introducing the DCS reagent, dip tube 26 is preferably purged with nitrogen or another non-reactive gas to prevent reaction of the reagents within the diptube and pluggage. After the reaction is conducted, the crude liquid contained within reactor vessel 20 is passed through filter 70 where the TBA.HCl by-product salt is collected on the surface of the filter forming a salt cake (not shown) and the filtered crude liquid containing BTBAS and TBS can be collected in flash vessel 40. Vacuum pump 90 may be used to facilitate the removal of the filtered crude liquid from the filter bed. A TBA rinse supplied from tank 60 may be used to further rinse any residual BTBAS from the salt cake. This TBA rinse may be also collected in vessel 40. The filtered crude liquid in vessel 40 may be heated via heating/cooling jacket 44 to a temperature at or slightly above the vaporization temperature of TBA or 45° C. to vaporize the TBA contained therein. The vaporized TBA is collected in receiver tank 30 and may be cooled via heating/cooling jacket 34 to provide liquid TBA. Vacuum pump 100 aids in the removal of the vaporized TBA from the filtered crude. The TBA in receiver tank 30 may be used as a supply source for reactor vessel 20. The filtered crude remaining in vessel 40 after the vaporized TBA is removed can be passed through filter 80 and collected. This filtered BTBAS crude may then be purified to extract the BTBAS product by any of the methods described herein.

The invention will be illustrated in more detail with reference to the following examples, but it should be understood that the present invention is not deemed to be limited thereto. The gas chromatograph ("GC") analyses were carried out on a 30 meter XT-5 column manufactured by J&W Scientific with a mass selective detector interface.

EXAMPLES

Comparative Example

Synthesis of Bis(tertiary-butylamino)silane Using THF as a Solvent

A reaction mixture containing 150 ml of the solvent tetrahydrofuran (THF) and 50 ml of TBA was charged into a 300 mL stainless steel reactor manufactured by Parr Instrument Co. of Moline, Ill. equipped with a magnetic stirrer. The reactor was connected to a stainless steel vacuum line equipped with two 300 cc stainless steel ballasts, pressure gauge, a soda-lime trap, and a vacuum pump. The reactor was purged with nitrogen and cooled to and maintained at a temperature of 24° C. throughout the reaction. A continuous amount of high purity (e.g., 99.8%) dichlorosilane (DCS) was fed as a vapor through a subsurface dip tube into the reaction mixture. The total amount of DCS consumed during the reaction was 10.1 grams. The reactor was sealed and allowed to warm to room temperature with stirring. After the reaction was completed, the reactor was vented and purged with $N_2$.

The reactor contents were poured through a 0.45 μm glass frit filter manufactured by Ace Glass to remove the TBA.HCl salt from the BTBAS-containing liquid. The solvent was removed from the BTBAS-containing liquid via rotary evaporation to provide a final concentrated product. The concentrated product was analyzed by GC analysis and found to contain the following: 0.40% TBA, 88.78% BTBAS, 0.45% 3-aza-2,2,8,8-tetramethyl-5-oxa-4,6-disilanane, 0.50% tris(tert-butylamino)silane, 0.94% bis{[(tert-butyl)amino]silamethyl}(tert-butyl)amine, 1.8% other impurities, and the remainder was assumed to be THF.

Example 1

Synthesis of Bis(tertiary-butylamino)silane (BTBAS) Using the TBA Reagent as a Solvent A 250 mL amount of anhydrous liquid tert-butylamine (TBA) was charged into a 300 mL stainless steel reactor manufactured by Parr Instrument Co. of Moline, Ill. equipped with a magnetic stirrer. The reactor was purged with nitrogen prior to introducing the TBA reagent. The reactor was connected to a stainless steel vacuum line equipped with two 300 cc stainless steel ballasts, pressure gauge, a soda-lime trap, and a vacuum pump. The reactor was cooled to −5° C. with a dry ice/acetone bath. A continuous amount of high purity DCS (e.g., 99.8%) was fed as a vapor through a subsurface dip tube into the TBA liquid to provide a reaction mixture. The total amount of DCS consumed during the reaction was 8.2 grams. The reaction mixture was stirred throughout the reaction. The reactor was sealed and heat from the reaction exotherm was removed through the reactor walls. After the reaction was completed, the reactor was vented and purged with $N_2$.

The product of the reaction was a BTBAS-containing crude liquid having a TBA.HCl salt contained therein. The liquid was analyzed by GC analysis and found to contain the following: 91.90% TBA, 7.34% BTBAS, 0.13% 3-aza-2,2,8,8-tetramethyl-5-oxa-4,6-disilanane, 0.012% tris(tert-butylamino)silane, 0.028% bis{[(tert-butyl)amino]silamethyl}(tert-butyl)amine, and 0.064% other impurities present in minor amounts.

Example 1 demonstrates that BTBAS can be synthesized using an excess amount of TBA as the solvent. No additional outside solvent is needed which eliminates process steps relating to the purification and drying of the solvent. Further, the potential for any unreacted DCS to remain within the solvent after the reaction is avoided.

Example 2

Distillation of BTBAS Crude

Crude BTBAS was prepared in accordance with the method described in Example 1. The crude BTBAS was distilled in a 1 inch×7 inch distillation column packed with stainless steel, 0.16"PROPACK™ having approximately 7 stages at a temperature of <100° C. and a pressure of <100 torr to obtain pure BTBAS from the crude liquid. At distillation temperatures and pressures, the TBA.HCl salt contained within the crude was found to disassociate and deposit in various parts of the distillation system thereby creating operating problems. Various fractions of the distillate were found to contain high amounts of chlorides or >1,500 ppm. Thus, the distillation process was adversely impacted by the presence of the TBA.HCl salt and the resulting BTBAS product had an undesirable level of chloride impurities remaining.

Example 3

Distillation of Filtered BTBAS Crude

Crude BTBAS was prepared in accordance with the method described in Example 1. The crude BTBAS was passed through a 0.45 μm glass frit filter manufactured by Ace Glass to remove the TBA.HCl salt from the liquid. A TBA rinse was used to remove any residual crude from the TBA.HCl filter cake. The TBA rinse was captured for use in subsequent reactions.

After filtration, the crude BTBAS was distilled in the same manner as described in Example 2. A negligible amount of TBA.HCl salt was observed in the condenser of the distillation column suggesting that a small amount of chloride precipitate may have escaped the 0.45 μm filter. However, this much salt did not pose operational issues and the resulting product had a chlorine level below 15 ppm. Compared to example 2, example 3 demonstrates that an effective filtration of the crude to remove the majority of the TBA.HCl salt contained within the crude BTBAS allows the crude BTBAS to be more effectively purified.

Example 4

Distillation of BTBAS Crude at 50 Torr Pressure

A batch distillation was conducted using 250 ml of BTBAS crude prepared in accordance with the method described in Example 1 and passed through a 0.45 μm fritted glass filter. The distillation was conducted in the same distillation system as examples 2 and 3. After establishing uniform conditions by operating the distillation column in total reflux, a reflux ratio of 0.5 was established. The distillation column was operated at 50 torr pressure. Reboiler temperature was increased from 30° C. to 86° C. until the end of distillation. All the product cuts contained >99.3% weight BTBAS as determined by GC analysis. No thermal decomposition was noted.

Example 4 demonstrates that purification by distillation at lower process temperatures and under vacuum conditions allows the crude BTBAS to be purified without affecting final product purity and minimizing thermal decomposition of the BTBAS product Example 5

Recycle of TBA from Prior Reactions

A 100 gallon stainless steel tank reactor equipped with stirrer was charged with 600 pounds of tert-butylamine (TBA). Approximately half of the charge was recycled t-butylamine that was recovered from previous synthesis reactions and remainder was fresh material. The reactor was cooled to 5–10° C. Gaseous dichlorosilane was fed to reactor through a subsurface dip tube over a period of 5.25 hours. A total of 45 lbs of dichlorosilane was reacted. The product was filtered using a Rosenmund filter/dryer. The filter cake was rinsed using the t-butylamine charge for the next reaction. The filter cake was dried under vacuum and the resulting condensate collected. The product was collected in a flash vessel where the excess t-butylamine was vacuum stripped. The product was filtered through a 1 micron polypropylene bag filter followed by a 0.45 micron polypropylene filter cartridge. The final BTBAS assay on a t-butylamine free basis was 99.5% and the TBA content was below 10%. This product was ready for final purification distillation.

While the invention has been described in detail and with reference to specific examples thereof, it will be apparent to one skilled in the art that various changes and modifications can be made therein without departing from the spirit and scope thereof.

What is claimed is:

1. A process for making an aminosilane, the process comprising reacting a stoichiometric excess of at least one amine selected from the group consisting of a secondary amine having the formula $(R^1)_2NH$, a primary amine having the formula $R^2NH_2$ or combinations thereof with at least one chlorosilane having the formula $(R^3)_nSiCl_{4-n}$ in the absence of an organic solvent under anhydrous conditions sufficient such that a liquid comprising the aminosilane product and an amine hydrochloride salt is produced and wherein $R^1$ and $R^2$ is each independently be a linear, cyclic or branched alkyl group having 1 to 20 carbon atoms; $R^3$ can be a hydrogen atom, an amine group, or a linear, cyclic or branched alkyl group having 1 to 20 carbon atoms; and n is a number ranging from 1 to 3.

2. The process of claim 1 further comprising:
   passing the liquid through a filter to provide an amine hydrochloride salt cake and a filtered liquid; and
   purifying the filtered liquid to provide the aminosilane product.

3. The process of claim 2 further comprising rinsing the amine hydrochloride salt cake with an amine.

4. The process of claim 3 wherein at least a portion of the amine in the reacting step is the amine rinse.

5. The process of claim 2 wherein the purifying step is at least one process selected from the group consisting of distillation, evaporation, membrane separation, extraction, and combinations thereof.

6. The process of claim 5 wherein the purifying process is distillation.

7. The process of claim 6 wherein the distillation is conducted at a pressure ranging from 40 to 100 torr.

8. The process of claim 7 wherein the distillation is conducted at a temperature ranging from 70 to 90° C.

9. The process of claim 1 wherein the amine is a secondary amine.

10. The process of claim 1 wherein the amine is a primary amine.

11. The process of claim 10 wherein the amine is tert-butylamine.

12. A process for making a bis(tertiarybutylamino)silane product, the process comprising:
    reacting tert-butylamine with dichlorosilane in the absence of an organic solvent under anhydrous conditions sufficient such that a liquid comprising the bis(tertiarybutylamino)silane product and a tert-butylamine hydrochloride salt is produced;
    passing the liquid through a filter to provide a tert-butylamine hydrochloride salt cake and a filtered liquid; and
    purifying the filtered liquid to provide the bis(tertiarybutylamino)silane product.

13. A process for making a bis(tertiarybutylamino)silane product having a chloride level of 15 ppm or below, the process comprising:
    reacting tert-butylamine with dichlorosilane in the absence of an organic solvent under anhydrous conditions sufficient such that a liquid comprising the bis(tertiarybutylamino)silane product and a tert-butylamine hydrochloride salt is produced;
    passing the liquid through a filter to provide a tert-butylamine hydrochloride salt cake and a filtered liquid;
    rinsing the tert-butylamine hydrochloride salt cake with tert-butylamine wherein at least a portion of the tert-butylamine rinse is used as at least a portion of the tert-butylamine in the reacting step; and
    purifying the filtered liquid to provide the bis(tertiarybutylamino)silane product.

14. The process of claim 13 wherein the purifying step is at least one process selected from the group consisting of distillation, evaporation, membrane separation, extraction, and combinations thereof.

15. The process of claim 14 wherein the purifying process is distillation.

16. The process of claim 15 wherein the distillation is conducted at a pressure ranging from 40 to 100 torr.

17. The process of claim 16 wherein the distillation is conducted at a temperature ranging from 70 to 90° C.

18. The process of claim 13 wherein the liquid in the reacting step further comprises tert-butylamine.

19. The process of claim 18 wherein the tert-butylamine is removed from the liquid by evaporation.

20. A process for making a bis(tertiarybutylamino)silane product comprising reacting a stoichiometric excess of tert-butylamine with dichlorosilane in the absence of an organic solvent under anhydrous conditions sufficient such that a liquid comprising the bis(tertiarybutylamino)silane product is produced.

* * * * *